(12) United States Patent
Bhatarah et al.

(10) Patent No.: US 8,541,399 B2
(45) Date of Patent: Sep. 24, 2013

(54) SOLVENT-BASED STERILISATION OF PHARMACEUTICALS

(75) Inventors: Parveen Bhatarah, Stevenage (GB); Kenneth Alan Greenwood, London (GB)

(73) Assignee: Resolution Chemicals Limited, Stevenage Hertfordshire (GB)

( * ) Notice: Subject to any disclaimer, the term of this patent is extended or adjusted under 35 U.S.C. 154(b) by 1927 days.

(21) Appl. No.: 10/505,137

(22) PCT Filed: Feb. 19, 2003

(86) PCT No.: PCT/GB03/00702
§ 371 (c)(1),
(2), (4) Date: Apr. 25, 2005

(87) PCT Pub. No.: WO03/070285
PCT Pub. Date: Aug. 28, 2003

(65) Prior Publication Data
US 2005/0222108 A1 Oct. 6, 2005

(30) Foreign Application Priority Data

Feb. 19, 2002 (GB) .................................. 0203912.1
Aug. 12, 2002 (GB) .................................. 0218724.3

(51) Int. Cl.
*A61K 31/56* (2006.01)
*A61K 31/58* (2006.01)
*A61K 9/14* (2006.01)

(52) U.S. Cl.
USPC ............ 514/169; 514/174; 514/177; 424/489

(58) Field of Classification Search
USPC ......................................................... 424/489
See application file for complete search history.

(56) References Cited

U.S. PATENT DOCUMENTS

| 3,962,430 | A | 6/1976 | O'Neill | |
|---|---|---|---|---|
| 4,105,550 | A | 8/1978 | Müller | |
| 4,263,253 | A | 4/1981 | Pilz et al. | |
| 4,899,914 | A | 2/1990 | Schweigl et al. | |
| 5,510,118 | A | 4/1996 | Bosch et al. | |
| 5,770,199 | A | 6/1998 | Eibl et al. | |
| 5,834,420 | A | 11/1998 | Laub et al. | |
| 5,914,122 | A | 6/1999 | Otterbeck et al. | |
| 6,068,816 | A | 5/2000 | Joseph | |
| 6,187,765 | B1 * | 2/2001 | Harris et al. | 514/172 |
| 6,392,036 | B1 | 5/2002 | Karlsson et al. | |
| 2002/0065256 | A1 | 5/2002 | Karlsson et al. | |

FOREIGN PATENT DOCUMENTS

| DE | 101 45 361 A1 | 4/2003 |
|---|---|---|
| EP | 0 008 454 | 3/1980 |
| EP | 0 197 554 B1 | 10/1986 |
| EP | 0 364 842 A1 | 4/1990 |
| EP | 0 525 502 B1 | 2/1993 |
| EP | 0 692 491 B1 | 1/1996 |
| EP | 0 722 344 B1 | 7/1996 |
| EP | 0 771 324 B1 | 5/1997 |
| GB | 2 374 013 A | 10/2002 |
| JP | 57-32212 | 2/1982 |
| JP | 62-114917 | 5/1987 |
| WO | WO 90/03782 A2 | 4/1990 |
| WO | WO 95/31964 A1 | 11/1995 |
| WO | WO 96/32095 A1 | 10/1996 |
| WO | WO 99/25359 A1 | 5/1999 |
| WO | WO 9925359 * | 5/1999 |
| WO | WO 99/34791 A1 | 7/1999 |
| WO | WO 99/36104 A2 | 7/1999 |
| WO | WO 99/51271 A2 | 10/1999 |
| WO | WO 00/25746 A2 | 5/2000 |
| WO | WO 02/072150 A2 | 9/2002 |
| WO | WO 03/028736 A2 | 4/2003 |

OTHER PUBLICATIONS

Ruch, F., et al., "Preparation of Micrometer Size Budesonide Particles by Precipitation," *J. Colloid Interface Sci.* 229:207-211, Academic Press (2000).
Patent Abstracts of Japan, English language abstract of JP 57-32212 (listed as document FP1 on accompanying form PTO/SB/08A).
Patent Abstracts of Japan, English language abstract of JP 62-114917 (listed as document FP3 on accompanying form PTO/SB/08A).
European Patent Office esp@cenet database, English language abstract of EP 0 525 502 B1 (listed as document FP8 on accompanying form PTO/SB/08A).
European Patent Office esp@cenet database, English language abstract of EP 0 692 491 B1 (listed as document FP9 on accompanying form PTO/SB/08A).
Unverified English language translation of DE 101 45 361 A1 (listed as document FP20 on accompanying form PTO/SB/08A).
International Search Report for International Application No. PCT/GB03/00702, European Patent Office, Netherlands, mailed on May 14, 2003.

* cited by examiner

*Primary Examiner* — Sreeni Padmanabhan
*Assistant Examiner* — Jody Karol
(74) *Attorney, Agent, or Firm* — Florek & Endres PLLC

(57) ABSTRACT

A sterile composition of a pharmaceutical compound is prepared by combining solvent with a non-sterile pharmaceutical compound to form a solution and filtering to yield a sterile pharmaceutical compound, optionally removing all or part of the solvent, and under sterile conditions combining the compound with a pharmaceutically acceptable carrier.

26 Claims, No Drawings

SOLVENT-BASED STERILISATION OF PHARMACEUTICALS

The present invention concerns a method for the sterilisation of drugs, in particular suspensions of drugs intended for use in nebulizers.

Previously it was acceptable for drugs intended for use in nebulizers to be prepared under "clean" conditions. Recently, however, the US FDA has implemented a requirement for all nebulizer solutions to be sterile.

In the light of the US FDA decision it is necessary to produce sterile suspension drugs in the US. This is emphasised by problems which have resulted from the use of "clean" suspensions. Multidose formulations made under "clean" conditions were previously acceptable in the US. However such formulations have caused problems in the US due to contamination.

Drugs typically provided as nebule suspensions are the steroids fluticasone and budesonide, used to treat asthma and chronic obstructive pulmonary disorder. These drugs are very insoluble in water and are sold as non-sterile powders.

A method of sterilising dry, powdered budesonide is known from International Publication Number WO 99/25359. The method of sterilisation is problematic as it requires budesonide powder to be sterilised and then be mixed with the other components of the formulation under sterile conditions. The drug formulation is subsequently made up under sterile conditions.

The sterilisation of suspensions raises particular problems. The desired biological activity of the formulation commonly requires that the diameter of particles of the drug lies within a narrow range (typically less than 5 micrometres). The standard means of sterilisation, that is the raising of the temperature of the formulation to 121° C. for 15 minutes, frequently destroys one or more of the components of the formulation. End sterilisation may alter particle size. In addition this treatment results in the clumping or agglomeration of the drug particles in the suspension such that the efficacy of the resulting product is impaired or abolished.

Known alternative methods for the sterilisation of pharmaceuticals are inappropriate for sterilizing suspension formulations of drugs. Pharmaceuticals may be sterilised by passage though a filter having a pore size of not more than 0.2 μm. However this cannot be used in the case of suspensions as the required particle size in these formulations is significantly greater than this filter pore size. Similarly, pharmaceuticals may generally be sterilised by gamma-irradiation, but budesonide, for example, is destroyed by such treatment. No further methods for the sterilisation of pharmaceuticals are currently acceptable to regulatory agencies.

JP 620114917 (Tokuo Saito) describes production of sterilised pills containing drugs and a solid carrier such as starch or wheat flour. The drugs are sterilised by immersing the non-sterile crude drug in 2-3 volumes of ethyl-alcohol for 24-48 hours. The end-product pills typically contain fewer than 10,000 micro-organisms and are produced without deterioration of the active ingredients.

JP 570032212 (Mitsui Toatsu Chem Inc) describes sterilisation of acetylsalicylic acid salts. The non-sterile salt is immersed in ethyl-alcohol for 1-5 hrs at 10-30° C. Crystals of the salts are filtered under sterile conditions, washed with more alcohol and dried under reduced pressure and low temperature to give the final product.

An object of the present invention is to provide an alternative and/or an improved method for sterilization of suspensions of pharmaceuticals.

Accordingly, the present invention provides a method for preparing a sterile composition of a pharmaceutical compound comprising combining solvent with a non-sterile pharmaceutical compound to yield a sterile pharmaceutical compound, optionally removing all or part of the solvent, and under sterile conditions combining the compound with a pharmaceutically acceptable carrier. In one aspect of the invention, the pharmaceutically acceptable carrier may comprise sterile water.

Hence, in use of the invention sterilization may be achieved by combining solvent with the previously non-sterile material. Optional other processing steps may be added, such as filtration as described in more detail below.

By "combining with", it is meant that solvent may be added to the compound to be sterilised, or vice-versa. Where solvent is added to the compound, solvent may be added drop-wise or all at once.

By sterile, it is meant that the resultant pharmaceutical composition meets the requirements of sterility enforced by medicine regulatory authorities, such as the MCA in the UK or the FDA in the US. Tests are included in current versions of the compendia, such as the British Pharmacopoeia and the US Pharmacopoeia.

In a particular embodiment the non-sterile pharmaceutical compound is a powder, for instance a micronized powder. This powder can be mixed with a solvent, forming a combination in which the effect of the solvent is to sterilize the active agent. A steroid in powdered form may be sterilized in this way and particular examples include budesonide or fluticasone.

Where the steroid to be sterilised is budesonide, it is preferred to carry out all processing steps under conditions of low light and low oxygen, in order to avoid degradation of budesonide.

Generally, any solvent with the required properties may be used in the invention either singly or in combination. A solvent suitable for use in the invention should preferably have the properties of high drug solubility, high solvent volatility (boiling point lower than that of water), and no, or few, water azeotropes, to ensure that large volumes of water are not lost during evaporation of the solvent. The US FDA guidance on "Q3C Impurities: Residual Solvents", Federal Register Vol 62 No. 247, page 67377 et seq classifies potentially suitable solvents according to their toxicity. International Committee for Harmonisation guidelines are set out in document no. CPMP/ICH/283/95. Class 1 solvents can be used, especially if processing steps enable complete removal of solvent from the final product. Neutral solvents and solvents having low toxicity are preferred, hence Class 2 or Class 3 solvents may preferably be used in the present invention. Suitable class 2 solvents are acetonitrile, chlorobenzene, chloroform, cyclohexane, 1,2-dichloroethane, dichloromethane, 1,2-dimethoxyethane, 1,4-dioxane, 2-ethoxyethanol, ethyleneglycol, formamide, hexane, methanol, 2-methoxyethanol, methylbutyl ketone, methylcyclohexane, N-methylpyrrolidone, nitromethane, tetrahydrofuran, toluene, 1,2-trichloroethene and xylene. Suitable class 3 solvents are acetone, anisole, 1-butanol, 2-butanol, butyl acetate, tert-butylmethyl ether, cumene, ethanol, ethyl acetate, ethyl ether, heptane, isobutyl acetate, isopropyl acetate, methyl acetate, 3-methyl-1-butanol, methylethyl ketone, methylisobutyl ketone, 2-methyl-1-propanol, pentane, 1-pentanol, 2-pentanol, 2-propanol, and propyl acetate. In certain embodiments, dependent upon drug chemistry, in order to avoid drug degradation such as hydrolysis, anhydrous, or minimal water content solvents are preferred. In certain other embodiments, it is particularly preferred that the solvent comprises an alcohol. Most particularly preferred is ethyl alcohol, since this solvent is already approved for pharmaceutical formulations for delivery to the lungs. Other alcohols, such as methyl alcohol and isopropyl alcohol, and non-alcohol solvents such as ethyl acetate and TBME may also be used.

Good results have been obtained by combining solvent with the compound at an elevated temperature, suitably from 20° C. below the boiling point of the solvent up to its boiling point. This can increase the amount of compound that dissolves and may decrease the dissolving time. Solvent can be combined with compound at reflux.

In an alternative aspect of the invention, the combining of solvent and compound to be sterilised is carried out at room temperature. To aid dissolving of the compound in the solvent, however, it may be advantageous to heat the solvent. In one embodiment of the present invention, the solvent is heated to 30-50° C. Good results have been obtained using solvent heated to about 40° C.

In one aspect of the invention sufficient solvent is used to obtain a slurry of the compound. Hence, there is insufficient solvent to form a solution of the compound, nevertheless sterilization is achieved. An advantage is that only a small quantity of solvent is used and where a minimal amount of solvent is tolerated in the final composition, the solvent added for the purpose of sterilization need not be removed to meet the criteria for acceptance of the final composition for pharmaceutical use.

Where solvent is removed from the sterilized composition and the compound is heat-sensitive, solvent is typically removed under reduced pressure, preferably under vacuum conditions, and preferably at a temperature of 40° C. or less. This avoids potential damage to the compound caused by exposure to heat. Following evaporation, typically only a few ppm of solvent will remain. If the solvent used is ethyl alcohol, it may be an option to omit this evaporation step, although this is dependent on the final concentration present and maximum allowed levels set by the regulatory bodies. In some cases, it may be essential to remove all solvent from the final composition, depending on the limits specified in the ICH guidelines. Where the compound is not heat-sensitive, solvent can be removed at elevated temperature and atmospheric pressure.

In a particular embodiment, removing solvent yields an essentially solvent-free, sterile powder, suitable for further processing in a sterile line or for packaging and disposal in this sterile form.

In an alternative aspect of the invention, sufficient solvent is used to dissolve the compound, thus obtaining a solution of the compound. For example, 15 or more volumes (measured with respect to weight of drug) of 96% ethanol may be used to dissolve budesonide and 60 or more volumes of ethanol, or 19 or more volumes of acetone to dissolve fluticasone.

Optionally, the solution is filtered. The purpose of filtration is as a further sterilisation step and to remove any biomass. Removal of non-viable biomass from the final formulation may not be essential—many pharmaceutical formulations undergo terminal sterilisation, without further filtering. If, therefore, the required level of sterility can be obtained simply by addition of solvent, the filtration step may be unnecessary.

Omitting the filtration step would also avoid the expense of replacing clogged filter membranes for every batch of drug solution prepared. In cases where addition of solvent results in incomplete sterilization the addition of a filtration step has the benefit of completing the sterilization.

It is an option for the filter, if present, to be sterile. A filter having a pore size of 0.2 µm or less is preferred.

In a yet further aspect of the invention, the sterile pharmaceutical compound is combined with water to form a suspension. If a sterile solution of the pharmaceutical compound is combined with water, the particles will precipitate out of solution to form a suspension. Alternatively, a sterile powder can be added directly to water.

The water will typically be sterile filtered and contain surfactant, such as polysorbate containing compounds, especially Tweens 20 and 80.

It is also an option to remove solvent from the suspension. This solvent may be residual from a sterile powder or may be present within the solution before it is combined with water. Where the compound is heat-sensitive, solvent is typically removed from the suspension under reduced pressure, preferably under vacuum conditions and preferably at a temperature of 40° C. or less. Where the compound is not heat-sensitive, solvent can be removed at elevated temperature and atmospheric pressure.

In order to be effective in the lungs, the particle size of the active ingredient, fluticasone and budesonide in specific embodiments of the invention, must be within a certain size range, and is likely to need to be reduced following preparation of a sterile composition as described. Hence, a still further aspect of the invention comprises treating the suspension to obtain a particle size distribution having a mass mean diameter less than 10 μm, preferably in the range 1-5 μm, most preferably 2-3 μm. The sterile suspension may, for instance, be passed through a homogenizer, microfluidiser or similar device to reduce the average mass median diameter of the particles, preferably pre-sterilised to avoid contamination of the sterile suspension. A suitable device, referred to as a Microfluidizer®, is available from Microfluidics, Inc., described in WO 99/07466.

Further treatments of the sterile suspension can include diluting the suspension with sterile water and/or adding excipients such as disodium EDTA and trisodium citrate, so as to obtain the end-product pharmaceutical formulation. Excipients can also be added at an earlier stage, e.g. prior to evaporating solvent or at the same time as adding surfactant or post particle-size reduction.

The sterile composition is then typically stored in sterile containers, most preferably ampoules. In a use of the invention, the ampoules are nebules. Preferably, the nebules are pre-sterilised and of the blow-fill-seal type.

A specific process similar to that used for the sterilisation and formulation of budesonide has been developed for fluticasone in such a way that it can be performed in the same process plant. This process involves dissolving in acetone, sterile filtration, quenching into aqueous surfactant, distillation to remove the acetone, microfluidisation and dilution/addition of excipients. In this process, the major differences between formulation of the fluticasone propionate and the budesonide include that fluticasone propionate is not reported to degrade on exposure to heat and light, and that fluticasone propionate appears to be chemically stable to distillation at 100° C. for at least 30 hours.

In one of the examples described below, the surfactant used to formulate sterile fluticasone propionate is Tween 20 rather than Tween 80. Less surfactant is used, and foaming problems observed in the budesonide process are not evident in the fluticasone propionate distillation. Faster distillation and higher process throughput are therefore possible.

The invention further provides a method for preparing a sterile composition of a pharmaceutical compound comprising combining solvent with a non-sterile pharmaceutical compound so as to form a solution and filtering the solution to yield a sterile solution of the pharmaceutical compound. It is an option to remove solvent from the sterile solution, for example, to yield a solvent-free powder. Alternatively, the sterile solution may be combined with water to form a suspension, from which solvent may be removed. Optional and preferred features of previously described embodiments of the invention apply equally to this embodiment.

The invention further provides a method for preparing a sterile composition of a pharmaceutical compound comprising combining solvent with a suspension of a non-sterile pharmaceutical compound to yield a sterile suspension of a pharmaceutical compound, removing solvent, and under sterile conditions combining the sterile suspension with a pharmaceutically acceptable carrier. In one embodiment of the invention, the pharmaceutically acceptable carrier may comprise sterile water.

The volume of solvent required to sterilise an aqueous suspension of drug will generally be greater than for sterilisation of a dry powder, therefore thorough evaporation from the suspension is required. Other preferred features of this method are as for the above-described methods of the invention.

The invention also provides a sterile composition of a pharmaceutical compound prepared by combining solvent with a non-sterile pharmaceutical compound to yield a sterile pharmaceutical compound, optionally removing all or part of the solvent, and under sterile conditions combining the compound with a pharmaceutically acceptable carrier.

The sterile composition may be a suspension or a powder.

The invention further provides an apparatus for preparing a sterile composition of a pharmaceutical compound, comprising a container defining a sterile inner compartment, a first vessel containing a solvent, and a second vessel containing a non-sterile pharmaceutical compound, arranged so that the solvent can be combined with the non-sterile compound to yield a sterile compound within the compartment, the compartment also containing a sterile aqueous solution into which the sterile compound can be introduced to form a sterile suspension, optionally an apparatus for alteration of the particle size distribution of the suspension and further optionally a sterile exit line for transfer of sterile suspension to sterile ampoules.

The apparatus may further comprise a sterile filter. Good results have been obtained when the sterile filter of the apparatus has a pore size of 0.2 µm or less.

A particular advantage of embodiments of the present invention is that sterilisation is carried out prior to particle size reduction, which enables particle size to be more precisely controlled.

The invention is now illustrated in specific embodiments by way of the following examples.

EXAMPLE 1

Sterilisation of Budesonide

Powdered budesonide was dissolved in 15 volumes of 96% alcohol, at reflux. The resultant hot solution was poured through a sterile Pall filter of pore size 0.2 µm to remove any biomass. 5 liters of sterile water/Tween 80 concentrate were added per liter of filtered drug solution, causing drug particles to precipitate out of solution, forming a suspension.

Evaporation of solvent from the suspension was then carried out at 40° C., under vacuum conditions. Further water was added and removed by distillation to ensure residual alcohol was kept to a minimum. Residual alcohol concentration was measured and the drug particle size distribution determined.

The concentrated suspension was passed though a microfluidiser, using a 100 µm reaction chamber, in order to reduce the average drug particle size to a mass mean diameter of 2-3 µm. Reaction chambers of gauge 110 µm, 87 µm and 75 µm "Y" and/or "Z" type either single or multi-pass may also be used, depending on the desired final particle size. The microfluidised suspension was diluted with sterile water—1 liter suspension being made up to 500 liters—and combined with disodium EDTA and trisodium citrate, as excipients for the final formulation. Standard, pre-sterilised nebules were filled with diluted drug suspension and sealed ready for use.

EXAMPLE 2

Alternative Sterilisation Method for Budesonide

Budesonide (36 g) was dissolved in de-gassed, pre-heated (35-40° C.) 96% ethanol (1.08 liters, 28 volumes) under nitrogen and protected from light at all times. A clear solution of budesonide was obtained and added drop-wise to a sterile-filtered aqueous solution (2.7 liters, 75 volumes) containing Tween-80 (14.4 g) disodium EDTA (7.21 g), at such a rate that would maintain a steady distillation of ethanol during the high vacuum. Distillation was carried out (30° C. maximum pot temperature, 40° C. maximum jacket temperature, 30-35 mb). A splash head was fitted to the flask as a precaution to avoid product being carried over in the possible event of foaming.

Upon completion of addition, the contents were stripped down to a volume of 750 ml. Further water (500 ml) was added before distilling down to a final volume of 30-35 volumes (1.25 liters, 34.7 volumes in this example) with respect to budesonide input.

The slurry was then transferred to an amber flask using minimal water to rinse the distillation flask (100 ml used in this example). This was then transferred to a Microfluidizer®, rinsing the flask with any remaining water (90 ml in this experiment) required to achieve a total volume of 40 volumes with respect to the weight of budesonide input (1440 ml), thus yielding a concentrated budesonide suspension.

EXAMPLE 3

Further Alternative Sterilisation Method for Budesonide

Ethanolic budesonide solution was obtained as described in Example 2.

Ethanolic budesonide solution was sterile filtered into the Tween/water at atmospheric pressure prior to any distillation. Upon completion of filtration, (there may be in addition a small alcohol wash) a suspension of budesonide in approximately 103 volumes alcohol/water/Tween-80 was obtained with respect to weight of budesonide input.

Distillation was commenced at 30° C. maximum pot temperature (40° C. maximum jacket temperature) and 62 volumes of alcohol/water were removed from the system to leave 41 volumes of water plus a small amount of alcohol. 25 volumes of water were sterile filtered into the batch and removed by vacuum distillation under the same temperature conditions. A further 25 volumes of water were sterile filtered into the batch and the process repeated to leave 41 volumes of a sterile suspension of budesonide in water/Tween.

The concentrated budesonide suspension was then microfluidised to a particle size of mass median diameter 2-3 µm.

The concentrated, microfluidised budesonide suspension was then transferred to the final filling tank and flushed through with enough sterile water to ensure complete transfer of batch. At this stage the additional excipients, namely disodium EDTA, trisodium citrate, citric acid, and sodium chloride, were sterile filtered into the system and flushed into the final product tank and the tank was made up to 600 L with sterile water. The final concentrations of the excipients in the formulation were as follows:

| Tri-sodium citrate | 0.5 g/L | 0.05% w/v |
|---|---|---|
| Citric acid | 0.28 g/L | 0.028% w/v |
| Sodium chloride | 8.5 g/L | 0.085% w/v |
| EDTA di-sodium salt | 0.1 g/L | 0.01% w/v |
| Tween-80 | 0.2 g/L | 0.02% w/v |

The diluted budesonide suspension was then transferred to sterile ampoules.

EXAMPLE 4

Fluticasone Propionate Sterilisation

The solubility of fluticasone propionate was measured by w/w % assay of saturated solutions in a variety of solvents at 21-23° C. The results are summarised in the table below.

| Solvent | w/w % solubility of fluticasone propionate |
|---|---|
| Acetone | 5.7 |
| Ethanol | 0.4 |
| tBME | 1.2 |
| Isopropanol | 0.3 |
| Ethyl acetate | 0.2 |

These results show that fluticasone propionate is significantly more soluble in acetone than in the other solvents tested. Acetone has numerous additional advantages including low toxicity (Class 3 solvent), low boiling point (56° C.) and lack of water azeotrope.

Fluticasone propionate (1 g) was dissolved with 19 volumes of acetone at 40° C. The solution was filtered and the filtrate was added to a mixture of purified water (50 ml) and Tween-20 (80 mg) to form a suspension.

The distillation to remove solvent was performed at 200 mbar, <40° C. Distillation was stopped after 20 mls of distillate were collected, at which point most of the water had also been removed. On dilution of the slurry, with water, to approximately 40 volumes, the residual acetone concentration was 165 ppm.

Particle size analysis of the final slurry showed a volume mean diameter of 11.11 μm.

Less processing is required to reduce the particle size than that required in the budesonide process of examples 1-3, in which the slurry had an initial particle size of over 50 μm.

The end formulation mixtures were as follows:—
0.25 mg/ml Concentration
Fluticasone Propionate—0.25 mg
Sorbitan Laurate—0.009 mg
Sodium Chloride—4.8 mg
Polysorbate 20 (Tween 20)—0.07 mg
Sodium acid phosphate (sodium dihydrogen phosphate dihydrate)—9.4 mg
Sodium phosphate dibasic anhydrous—1.75 mg
1.0 mg/ml Concentration
Fluticasone Propionate—1.0 mg
Sorbitan Laurate—0.01 mg
Sodium Chloride—4.8 mg
Polysorbate 20 (Tween 20)—0.08 mg
Sodium acid phosphate (sodium dihydrogen phosphate dihydrate)—9.4 mg
Sodium phosphate dibasic anhydrous—1.75 mg

EXAMPLE 5

Further Fluticasone Propionate Sterilisation

In this example, a development of example 4, the distillation was performed at atmospheric pressure and the first distillation was halted when the pot temperature reached 99° C. This procedure resulted in an acceptable acetone content of approximately 1.25 ppm in the formulated product. A further 25 volumes of water were added and the distillation continued until 25 volumes of distillate had been removed.

The acetone concentration in the slurry was found to be 2241 ppm after the first distillation and 74 ppm after the second distillation. The HPLC area % profile was unchanged from the starting solid to the final aqueous slurry, indicating that fluticasone propionate is stable to distillation at 100° C.

EXAMPLE 6

Fluticasone Propionate Formulation

This example was carried out as in Example 5, except that addition and further distillation of water was continued to assess the lowest final acetone level achievable by this method. After initial distillation up to a pot temp of 100° C. (24 vols of distillate) 25 vols of water was added and the distillation was continued until a further 25 vols of distillate were removed. This was performed 3 times and the acetone concentration at each stage is summarised in the table below.

| Sample | Acetone Conc. (ppm) |
|---|---|
| Slurry after $1^{st}$ distillation (to 100° C.) | 337 |
| Slurry after $1^{st}$ additional water distillation | 46 |
| Slurry after $2^{nd}$ additional water distillation | 61 |
| Slurry after $3^{rd}$ additional water distillation | 25 |

An acetone concentration of 25 ppm at this stage corresponds to an acetone concentration of 1.25 ppm after dilution down to the formulated product concentration.

EXAMPLE 7

Fluticasone Propionate Stability

A sample from the above example was heated to 100° C. under nitrogen for 30 hours to examine the stability of the drug under extended distillation times required on scale-up. The results of the stability study are summarised in the table below.

| Time (hr) | Area % |
|---|---|
| 0 | 99.2 |
| 6 | 99.4 |
| 24 | 99.5 |
| 30 | 99.4 |

No new impurities were evident in the area % chromatogram and the assay of the fluticasone propionate appears unaffected by extended periods at 100° C. in water.

The invention claimed is:

1. A method for preparing a sterile pharmaceutical composition of a steroid comprising:
   (i) dissolving a non-sterile steroid in a non-aqueous solvent to yield a solution of the steroid,
   (ii) filtering the solution of (i) to yield a sterile solution,
   (iii) combining the sterile solution of (ii) with sterile water to form a sterile aqueous suspension,
   (iv) treating the sterile aqueous suspension of (iii) to obtain a sterile aqueous suspension with a particle size distribution having a mass median diameter less than 10 μm,
   (v) under sterile conditions combining the sterile aqueous suspension of (iv) with a pharmaceutically acceptable carrier to yield a sterile pharmaceutical composition comprising a sterile aqueous suspension of the steroid having a mass median diameter less than 10 μm, and
   (vi) storing the sterile pharmaceutical composition of (v) in sterile containers.

2. The method of claim 1, wherein the non-sterile steroid is a powder.

3. The method of claim 2, wherein the powder is a micronized powder.

4. The method of claim 1, wherein the steroid is budesonide.

5. The method of claim 1, wherein the solvent comprises an alcohol.

6. The method of claim 1, wherein the solvent comprises a Class 3 solvent.

7. The method of claim 1, wherein the solvent comprises a Class 2 solvent.

8. The method of claim 1, comprising combining solvent with the steroid at a temperature from 20° C. below the boiling point of the solvent up to its boiling point.

9. The method of claim 1, wherein the solvent is at reflux.

10. The method of claim 1, comprising filtering the solution through a filter having a pore size of 0.2 μm or less.

11. The method of claim 1, wherein the sterile water contains a surfactant.

12. The method of claim 1, comprising treating the suspension to obtain a particle size distribution having a mass median diameter in the range 1-5 μm.

13. The method of claim 12, comprising treating the suspension to obtain a particle size distribution having a mass median diameter in the range 2-3 μm.

14. The method of claim 1, comprising storing the sterile composition in sterile ampoules.

15. A method for preparing a sterile suspension of budesonide, comprising:
   (i) dissolving non-sterile budesonide in a non-aqueous solvent to yield a budesonide solution,
   (ii) filtering the solution of (i) to yield a sterile solution,
   (iii) combining the sterile solution of (ii) with sterile water to form a sterile aqueous suspension of budesonide,
   (iv) treating the sterile aqueous suspension of (iii) to obtain a sterile aqueous suspension with a particle size distribution having a mass median diameter less than 10 μm,
   (v) under sterile conditions combining the sterile aqueous suspension of (iv) with a pharmaceutically acceptable carrier to yield a sterile pharmaceutical composition comprising the sterile aqueous suspension of budesonide having a mass median diameter less than 10 μm, and
   (vi) storing the sterile pharmaceutical composition of (v) in sterile containers.

16. The method of claim 15, wherein the solvent comprises an alcohol.

17. The method of claim 15, comprising filtering the solution through a filter having a pore size of 0.2 μm or less.

18. The method of claim 17, comprising treating the suspension to obtain a particle size distribution having a mass median diameter in the range 1-5 μm.

19. The method of claim 17, comprising treating the suspension to obtain a particle size distribution having a mass median diameter in the range 2-3 μm.

20. A method for preparing a sterile pharmaceutical composition of a steroid comprising:
   (i) dissolving a non-sterile steroid in a non-aqueous solvent to yield a solution of the steroid,
   (ii) filtering the solution of (i) to yield a sterile solution,
   (iii) combining the sterile solution of (ii) with sterile water to form a sterile aqueous suspension,
   (iv) removing all or part of the non-aqueous solvent from the sterile aqueous suspension of (iii) to yield a sterile aqueous suspension having reduced non-aqueous solvent content,
   (v) treating the sterile aqueous suspension having reduced non-aqueous solvent content of (iv) to obtain a sterile aqueous suspension with a particle size distribution having a mass median diameter less than 10 μm,
   (vi) under sterile conditions combining the sterile aqueous suspension of (v) with a pharmaceutically acceptable carrier to yield a sterile pharmaceutical composition comprising a sterile aqueous suspension of the steroid having a mass median diameter less than 10 μm, and
   (vii) storing the sterile pharmaceutical composition of (vi) in sterile containers.

21. A method for preparing a sterile pharmaceutical composition of budesonide comprising:
   (i) dissolving a non-sterile budesonide in a non-aqueous solvent to yield a budesonide solution,
   (ii) filtering the solution of (i) to yield a sterile solution,
   (iii) combining the sterile solution of (ii) with sterile water to form a sterile aqueous suspension of budesonide,
   (iv) removing all or part of the non-aqueous solvent from the sterile aqueous suspension of (iii) to yield a sterile aqueous suspension having reduced non-aqueous solvent content,
   (v) treating the sterile aqueous suspension having reduced non-aqueous solvent content of (iv) to obtain a sterile aqueous suspension with a particle size distribution having a mass median diameter less than 10 μm,
   (vi) under sterile conditions combining the sterile aqueous suspension of (v) with a pharmaceutically acceptable carrier to yield a sterile pharmaceutical composition comprising a sterile aqueous suspension of budesonide having a mass median diameter less than 10 μm, and
   (vii) storing the sterile pharmaceutical composition of (vi) in sterile containers.

22. The method of claim 15, comprising storing the sterile composition in sterile ampoules.

23. The method of claim 20, comprising storing the sterile composition in sterile ampoules.

24. The method of claim 21, comprising storing the sterile composition in sterile ampoules.

25. The method of claim 20, comprising removing solvent under reduced pressure.

26. The method of claim 20, comprising removing solvent at atmospheric pressure.

* * * * *